(12) United States Patent
Kuperus et al.

(10) Patent No.: US 7,229,603 B2
(45) Date of Patent: Jun. 12, 2007

(54) STABLILIZED AND LYOPHILIZED RADIOPHARMACEUTICAL AGENTS

(75) Inventors: John H. Kuperus, Tampa, FL (US); Robert G. McKenzie, Jr., Tampa, FL (US); Brooke Schumm, III, Ellicott City, MD (US)

(73) Assignee: AnazaoHealth Corporation, Tampa, FL (US)

( * ) Notice: Subject to any disclaimer, the term of this patent is extended or adjusted under 35 U.S.C. 154(b) by 0 days.

(21) Appl. No.: 10/904,099

(22) Filed: Oct. 22, 2004

(65) Prior Publication Data

US 2005/0281737 A1 Dec. 22, 2005

Related U.S. Application Data

(60) Provisional application No. 60/522,619, filed on Oct. 20, 2004, provisional application No. 60/608,060, filed on Sep. 8, 2004, provisional application No. 60/580,455, filed on Jun. 17, 2004.

(51) Int. Cl.
  *A61K 51/00* (2006.01)
  *A61M 36/14* (2006.01)

(52) U.S. Cl. .................. 424/1.65; 424/1.11; 424/1.49; 424/1.81; 424/9.1

(58) Field of Classification Search ................ 424/1.11, 424/1.65, 1.49, 1.69, 9.1, 1.81, 1.85, 1.89; 534/7, 10–16
See application file for complete search history.

(56) References Cited

U.S. PATENT DOCUMENTS

| | | | |
|---|---|---|---|
| 2,066,302 A | 12/1936 | Reichel | |
| 2,099,659 A | 11/1937 | Reichel | |
| 2,149,304 A | 3/1939 | Masucci | |
| 3,981,980 A | 9/1976 | Baker et al. | |
| 4,229,427 A | 10/1980 | Whitehouse | |
| 4,452,774 A | 6/1984 | Jones | |
| 4,489,053 A | 12/1984 | Azuma | |
| 4,652,440 A | 3/1987 | Paik | |
| 4,707,544 A | 11/1987 | Jones | |
| 4,735,793 A | 4/1988 | Jones | |
| 4,778,672 A | 10/1988 | Deutsch | |
| 4,826,961 A | 5/1989 | Jones | |
| 4,872,561 A | 10/1989 | Jones | |
| 4,885,100 A | 12/1989 | Iqbal | |
| 4,894,445 A | 1/1990 | Carpenter | |
| 5,150,394 A | 9/1992 | Karellas | |
| 5,219,556 A * | 6/1993 | Wolfangel | ................ 424/1.53 |
| 5,324,824 A | 6/1994 | Carpenter | |
| 5,468,355 A | 11/1995 | Shefer | |
| 5,693,324 A | 12/1997 | Edwards | |
| 5,739,313 A | 4/1998 | Collins | |
| 5,985,240 A | 11/1999 | Zamora et al. | |
| 6,024,938 A | 2/2000 | Corbo et al. | |
| 6,428,768 B1 | 8/2002 | DeRosch et al. | |
| 6,750,037 B2 | 6/2004 | Adair | |

OTHER PUBLICATIONS

Wahl R et al, Inhibition of autoradiolysis of radiolabeled monoclonal antibodies by cryopreservation, 31(1) J. Nucl. Med. 84-89 (Socy. Nucl. Med. 1990).
Pandey PM, Formulation and evaluation of a two-components lyophilized kit for Tc-sestamibi: Transchelation preparation of Tc-99m-sestamibi (abstract only), 24(7) Nucl. Med. And Biol. 697-700 (Oct. 1997).
Mushtaq A, Formulation of 99m Tc-Sc-EDTMP: Freeze-Dried Kit for Bone Scanning, 25(3) Nucl. Med. And Biol. 313-315 (Apr. 1998).
Meares C et al, Conjugation of Antibodies with Bifunctional Chelating Agents: Isothiocyanate and Bromoacetamide Reagents, Methods of Analysis, and Subsequent Addition of Metal Ions, 142 Anal. Biochemistry, 68-78 (1984).
Mather S et al., 28(6) J. Nucl. Med. 1034-1036 (1987).
Rey, Louis and May, Joan C., editors, Freeze-Drying/Lyophilization of Pharmaceutical and Biological Products, Preface, pp. iii-v, 1-30, 473-477 (Marcel Dekker, Inc., New York, Basel 1999 (Nat'l Library of Medicine Call No. W1 DR893B v. 96 1999)).
Visser et al., Optimal quality (131) I-monoclonal antibodies on high-dose labeling in a large reaction volume and temporarily coating the antibody with IODO-GEN, Abstract, J. Nucl. Med. 42(3): 509-19 (Socy. N. Med. Mar. 2001).
Johansson, A et al, Stability and Immunoreactivity of the Monoclonal Anticytokeratin Antibody TS1 after Different Degrees of Iodination, Abstract, Acta Oncologica 38(3):329-334 (May 1999).
Patent Cooperation Treaty International Search Report and Opinion-PCT/US2005/021561 mailed Sep. 28, 2005.
Patent Cooperation Treaty International Search Report and Opinion-PCT/US2005/021565 mailed Sep. 28, 2005.

* cited by examiner

*Primary Examiner*—Dameron L. Jones
(74) *Attorney, Agent, or Firm*—Brooke Schumm, III; Daneker, McIntire, Schumm et al.

(57) ABSTRACT

A novel method is set out of preparation of radioactive diagnostic radiopharmaceutical in a stable, shippable, lyophilized form by an apparatus designed to rapidly flash freeze and dehydrate a radiopharmaceutical composition to minimize auto radiolysis. The method proposes rapid cooling and removal of ambient vapor, and then ultra cold removal when the potential of explosive liquid oxygen is eliminated. The radioactive diagnostic radiopharmaceutical requires no further cold or refrigerated storage, including with respect to shipping, subsequent to stabilization. The preferred composition can be reconstituted "on site" by the addition of a suitable diluent to bring the radiopharmaceutical complex into solution at a desired concentration.

67 Claims, No Drawings

STABLILIZED AND LYOPHILIZED RADIOPHARMACEUTICAL AGENTS

CONTINUATION DATA

This application claims benefit to provisional application 60/580,455, filed Jun. 17, 2004; provisional application 60/608,060 filed Sep. 8, 2004; and provisional application 60/522,619 filed Oct. 20, 2004.

FIELD OF THE INVENTION

The present invention relates to the method of preparation and stabilization of a diagnostic or therapeutic radiopharmaceutical useful, for example, in mammalian imaging and cancer detection, and resulting composition. In particular, the present invention relates to the novel method of preparation of radioactive diagnostic radiopharmaceutical in a stable, shippable, lyophilized form by an apparatus designed to rapidly flash freeze and dehydrate a radiopharmaceutical composition to minimize auto radiolysis, the novelty centering on rapid cooling and removal of ambient vapor, and then ultra cold removal when the potential of explosive liquid oxygen is eliminated. The radioactive diagnostic radiopharmaceutical requires no further cold or refrigerated storage, including with respect to shipping, subsequent to stabilization. The preferred composition can be reconstituted "on site" by the addition of a suitable diluent to bring the radiopharmaceutical complex into solution at a desired concentration at the time of administration to the patient in need of a therapeutic or diagnostic radiopharmaceutical.

SUMMARY OF THE INVENTION

The present invention is directed to a stable radioactive diagnostic radiopharmaceutical composition that may be formed without stabilization additives and to a method of preparing such a composition. Stabilization additives may be added. Traditional techniques for freeze-drying (lyophilization) are subject to the lengthy crystal formation time of water. The composition is formed by avoiding that lengthy crystal formation time and the concurrent loss of diagnostic specificity due to autoradiolysis of the radiopharmaceutical. The length of traditional freeze-drying techniques and loss of diagnostic specificity due to autoradiolysis interfere with the technical accuracy necessary for nuclear medicine.

The novel technique of the inventors involves utilization of flash freeze techniques along with increasing the cold-exposed surface area and then rapidly decreasing the vapor pressure as well as super cold freeze drying of the radiopharmaceutical composition, the combination of which results in extremely rapid freeze-drying/lyophilization, enabling use of higher concentrations of radionuclides in the small scale amounts used in radiopharmaceutical imaging without damaging the ligands.

The preferred composition results from forming a complex between a gamma emitting radionuclide and a ligand in a suitable solvent, generally an aqueous solution and then lyophilizing the solution by use of small quantities in large surface area vessels at vacuum pressure in conjunction with rapid sub-zero cooling. The lyophilized radiopharmaceutical composition is shipped and stored and is often reconstituted "on site" by the addition of a suitable diluent to bring the radiopharmaceutical complex into solution at the time of administration to the patient in need of a therapeutic or diagnostic radiopharmaceutical. The present invention further is directed to stable radioactive diagnostic radiopharmaceutical compositions prepared by this method.

BACKGROUND OF THE INVENTION

With the invention of the Gamma Camera, and, just as importantly, with the invention of better high-speed imaging machines, pharmaceutical substances with radioactive "tags" have become extremely important in medical imaging and treatment. The concept is that a compound, or just as often, a part of a compound, called a ligand, sometimes referred to as an "agent" or which bonds to some other substance, is designed to target a particular area of a mammal's body or a particular type of tissue or molecule in that body. The compound, ligand or agent will be referred to as a ligand for convenience sake. The mammal this is most often used on is the human body, and references in this invention to a human are equally applicable to any mammal, or for that matter to any animal or plant.

For instance, certain ligands tend to concentrate in heart muscle tissue. The concept behind radiopharmaceutical imaging is to "tag" that ligand with a radioactive substance, i.e. radioactively mark a substance to create an "imaging agent," so that a health care provider can find out where the ligand exists or is concentrating. By administering the radioactively tagged ligand, and placing the patient in an imaging machine, a health care provider can "look inside" a patient's body to assist in therapy or diagnosis. If a person has poor heart circulation, the radionuclide tagged ligand, such as Tc 99m TIBI, will not be well-circulated to areas of the heart muscle which have compromised blood flow, enabling evaluation of a person's "heart condition." Importantly, the health care provider can often "look inside" without having to actually cut open or invade the body (non-invasive technique), or can minimize bodily invasion. Obviously, the continued presence of radioactive substances is not desirable, so substances are selected with a short "half-life." The half-life is a time defined as the time in which the radioactive emission declines by one-half. The diminution of radioactivity is referred to as radioactive decay. Between the body washing out the radiopharmaceutical substances used in conjunction with this invention, and the use of substances with a short half-life, the amount of a patient's radioactive exposure is minimized.

Radioactive pharmaceuticals are in common use in imaging studies to aid in the diagnosis of a wide variety of illnesses including cardiac, renal and neoplastic diseases. These pharmaceuticals, known in the art as "imaging agents," typically are based on a gamma-emitting radionuclide attached to a carrier molecule or "ligand." Gamma-emitting radionuclides are the radionuclides of choice for conducting diagnostic imaging studies because, while gamma emitting radiation is detectable with appropriate imaging equipment, it is substantially less-ionizing than beta or alpha radiation. Thus, gamma emitting radiation causes minimal damage to targeted or surrounding tissues.

Radioactive pharmaceuticals now are finding increased use as diagnostic agents for finding neoplastic disorders, especially tumors. Diagnostic radiopharmaceuticals generally incorporate a gamma emitting radionuclide, the radiation emission being useful in the detection of certain neoplastic disorders.

The radioactive marking or tagging is often done by complexing the radioactive substance inside a group of ligands, that is surrounding it by a complex of ligands, so that the desired chemical characteristics are expressed toward the exterior of the complex with the tag shielded by the outer complex and simply carried along as a marker. The entire complex with the radioactive element, also called a radionuclide, functions as a radioactive marker, and can be more generally referred to as a radiopharmaceutical.

The use of small quantities of drugs used for such activities is desirable for cost reasons, and it is desirable to minimize the amount of radioactive substance used.

While the efficacy of radioactive diagnostic and therapeutic agents is established, it is also well known that the emitted radiation can cause substantial chemical damage or destabilization to various components in radiopharmaceutical preparations, referred to as autoradiolysis. Emitted radiation causes the generation of free radicals in water solutions, which free radicals are generally peroxides and superoxides. Such free radicals can precipitate proteins present in the preparations, and can cause chemical damage to other substances present in the preparations. Free radicals are molecules with unbonded electrons that often result because the emissions from the radioactive element can damage molecules by knocking apart water molecules forming hydroxyl radicals and hydrogen radicals, leaving an element or compound with a shell of charged electrons which seek to bond with other molecules and atoms and destabilize or change those molecules and atoms. The degradation and destabilization of proteins and other components caused by the radiation is especially problematic in aqueous preparations. Under the present art, the radiolysis causes the aqueous stored ligand and radioactive isotope bonded to the ligand to degenerate and destroys the complex which renders it useless for imaging because the biological characteristics that localize the complex to a tissue are gone. The degradation or destabilization lowers or destroys the effectiveness of radiopharmaceutical preparations, and has posed a serious problem in the art. Wahl, et al, Journal of Nuclear Medicine, Vol 31, Issue 1 84-89, discuss the fact that freezing radiolabeled antibodies at −70 degrees C. stabilizes the molecule for an indefinite period but 80 to 90% of the immunoreactivity is lost in as little as 24 hours when stored at 4 degrees C.

If the ligands are permitted to reside with the radioactive elements for an extended period, particularly in an aqueous (water-based) solution, the radiolysis is increased. Thus, any process to reduce the compounds to dried form has to be rapid and yield predictable result. Further, to avoid the higher concentrations and protect the ligands, presently the radiopharmaceutical solution is diluted, but that in itself only slows the drying time and complicates the problem and increases the unpredictability of the non-radioisotope portion of the radiopharmaceutical because of radiolysis. Heating the radiopharmaceutical in solution to accelerate the drying and removal of water has the undesirable effect of potentially damaging the ligand since chemical activity normally increases upon heating or injection of energy and therefore the effects of radiolysis are also increased during this prolonged drying period with heating. Most proteins are badly damaged upon heating. Certain ligands, such as isonitrile, simply evaporate and disappear upon heating. Further, minimization of localized heating at an atomic scale is important to preserve both the small quantities needed and to yield a specific concentration of desired product.

Wolfangel, U.S. Pat. No. 5,219,556, Jun. 15, 1993, entitled stabilized therapeutic radiopharmaceutical complexes, expressed his concern as follows: "The isotopes which are most useable with this process are determined by practical considerations. Again, Tc-99m would be a poor candidate for use since its six-hour half-life makes lyophilization impractical, as the lyophilization step itself generally takes about 24 hours to perform."

Facially, the '556 invention seemed to identify a useful process and resulting composition, but the lyophilization step in '556 invention, as the application stated, took about 24 hours. The '556 invention stated: "The lyophilization is carried out by pre-freezing the product, and then subjecting the frozen product to a high vacuum to effect essentially complete removal of water through the process of sublimation. The resultant pellet contains the complex in an anhydrous form which generally can be stored indefinitely, with practical consideration being given to the half-life of the radionuclide. The intended period of storage for radiopharmaceutical products is thus practically limited by the half-life of the radionuclides. In the case of Re-186, for example, the desired period of storage would range from 7 to about 30 days. Thus, this pellet can be shipped to the end users of the product and reconstituted with a diluent at the time of administration to the patient with very little effort on the part of the health care professional and/or nuclear pharmacist."

Because the procedures in '556 did not rapidly lyophilize the product, and contemplated a 24 hour period for lyophilization, the claims of '556 invention were necessarily limited to utilization of a "therapeutic amount of an alpha- or beta-emitting radionuclide." Wolfangel had observed that compounds with a half-life of at least 12 hours are preferred. By contrast, the use of Tc-99m, which also emits gamma rays, with a half-life of only six hours, or the use of other similarly short-lived radioisotopes, becomes impractical.

Wolfangel '556 proposed in his example 1 to first lyophilize certain compounds, add the radionuclide complex, sparge with gas, seal the vial and then heat it. Unfortunately, the heating to 100 degree C. renders the procedure useless in conjunction with most proteins or peptides, and many commonly used complexes. Further, the proposal was to use 1 ml of sodium perrhenate Re-186 containing 1 mg of rhenium, with water added to produce 3 ml. The quantities contemplated were substantial and exposed the workers to substantial amounts of radiation. In example 3, it was proposed that the complex be frozen to −30 degree C. or colder and then apply a vacuum, but it was proposed to apply shelf heat at 6 degree per hour until a product temperature of 30 degree C. was reached, at which time the temperature would be held for two hours. That would require 12 hours. The procedure suffered from the infirmity of not quickly removing water and therefore not preventing radiolysis of the water and not preventing the generation of free radicals which damage the complexes. The second example 2 followed the first, but used smaller quantities, and proposed heating. Example 3 proposed heating to 85 degree C. for 30 minutes which would destroy most proteins and thereafter freezing and lyophilizing the sealed vials.

For diagnostic imaging purposes, radiopharmaceuticals based on a coordination complex comprised of a gamma-emitting radionuclide and a chelate have been used to provide both negative and positive images of body organs, skeletal images and the like. The Tc-99m skeletal imaging agents are well-known examples of such complexes. One drawback to the use of these radioactive complexes is that while they are administered to the patient in the form of a solution, neither the complexes per se nor the solutions prepared from them are overly stable. Consequently, the coordination complex and solution to be administered commonly are prepared "on site," that is, they are prepared by a nuclear pharmacist or health care technician just prior to conducting the study. The preparation of appropriate radiopharmaceutical compositions is complicated by the fact that several steps may be involved, during each of which the health care worker must be shielded from the radionuclide.

The preparation of stable radiopharmaceutical diagnostic agents, due to the type of radioactivity, presents even greater problems. These agents typically are based on a relatively energetic gamma emitting radionuclide complexed with a chelate. Frequently, the radionuclide/chelate complex is in turn bound to a carrier molecule which bears a site-specific receptor. Thus, it is known that a gamma emitting radionuclide attached to a tumor-specific antibody or antibody fragment can destroy targeted neoplastic or otherwise diseased cells via exposure to the emitted ionizing radiation. Bi-functional chelates useful for attaching a diagnostic radionuclide to a carrier molecule such as an antibody are known in the art. See e.g. Meares et al., Anal. Biochem. 142:68-78 (1984).

For most imaging and diagnostic applications of radiopharmaceutical complexes of the types mentioned above, the nonradioactive portion(s) of the complex is prepared and stored until time for administration to the patient, at which time the radioactive portion of the complex is added to form the radiopharmaceutical of interest. For example, attempts to prepare radionuclide-antibody complexes have resulted in complexes which must be administered to the patient just after preparation because, as a result of radiolysis, immunoreactivity may decrease considerably after addition of the radionuclide to the antibody. In Mather et al., J. Nucl. Med., 28:1034-1036 (1987), a technique for labeling monoclonal antibodies with large activities of radio iodine using the reagent N-bromosuccinimide is described. The authors suggest that the antibodies labeled in this manner be administered to the patient immediately after preparation to avoid losses of immunoreactivity. Other examples of the preparation of the nonradioactive portion of the complex followed by on-site addition of the radioactive portion are disclosed in U.S. Pat. No. 4,652,440 (1987). Further, in many situations, the radioactive component of the complex must be generated and/or purified at the time the radiopharmaceutical is prepared for administration to the patient. U.S. Pat. No. 4,778,672 (1988) describes, for example, a method for purifying pertechnetate and perrhenate for use in a radiopharmaceutical.

According to Wolfangel '556, EP 250,966 (1988) describes a method for obtaining a sterile, purified, complexed radioactive perrhenate from a mixture which includes, in addition to the ligand-complexed radioactive perrhenate, uncomplexed ligand, uncomplexed perrhenate, rhenium dioxide and various other compounds. Specifically, the application teaches a method for purifying a complex of rhenium-186 and 1-hydroxyethylidene diphosphonate (HEDP) chelate from a crude solution. Because of the instability of the complex, purification of the rhenium-HEDP complex by a low pressure or gravity flow chromatographic procedure is required. The purification procedure involves the aseptic collection of several fractions, followed by a determination of which fractions should be combined. After combining the appropriate fractions, the fractions are sterile-filtered and diluted prior to injection into the patient. The purified rhenium-HEDP complex should be injected into the patient within one hour of preparation to avoid the possibility of degradation. The rhenium complex may have to be purified twice before use, causing inconvenience and greater possibilities for radiation exposure to the health-care technician.

While the lyophilization process has been applied to various types of pharmaceutical preparations in the past, the notion of lyophilizing short lived gamma emitting radiopharmaceutical preparations has not been addressed. In part, this is believed to be due to skepticism of those skilled in the art that such a procedure could be safely carried out. U.S. Pat. No. 4,489,053 (Azuma et al.; Dec. 18, 1984) relates to Tc-99m-based diagnostic imaging agents. The patentee notes that the non-radioactive agents may be prepared in lyophilized form and that stabilizers are required to prevent radiolysis once the Tc-99m is added.

Thus, there is a need in the art for a method of centrally preparing and purifying a stabilized diagnostic radiopharmaceutical for shipment to the site of use in a form ready for simple reconstitution prior to its administration in diagnostic applications without the necessity of additional stabilizers. Because of the length of the Wolfangel process, many of the protein combinations with radionuclides are impractical because of the sensitivity of the protein in combination to any free radical attack caused by radioactive decay, and thus the present invention is a novel means to enable practical commercial use of radionuclide labelled proteins and peptides. The length also effectively prohibits the use of shorter half life radionuclides because in order to use them with the Wolfangel process, the concentrations of the radionuclides have to be increased to account for the several half lives during the 24 hours lyophilization and the time for shipment, which concentration exposes workers to higher concentrations of radioactivity and which time exposes the ligands to radiolysis which decreases their predictability of use in the patient, if they are effective at all. If, in order to avoid the higher concentrations, more dilute amounts are used, then the quantity of liquid involved jeopardizes the efficacy of lyophilization. There is a particular need in the art for a method of centrally preparing and purifying radionuclide-labeled antibodies and antibody fragments, owing to their relatively unstable immunoreactivities once in aqueous solution. Most particularly, this invention enables the use of short-half-life radionuclides with ligands potentially subject to radiolysis that are stable with useful shelf life at room temperatures that can be shipped in a commercially cheaper manner, and easily reconstituted.

OBJECTIVES OF THE INVENTION

An object of the invention is to accelerate the removal of water to minimize the peroxidation-related effects of radiolysis because of the accelerated removal of water which facilitates stabilization and predictability of concentration of a ligand or non-radioactive portion of a radiopharmaceutical because of reduced radiolysis.

An object of the invention is to use the minimization of peroxidation-related effects to improve the preservation of the chemical substituent complexes typically surrounding a radionuclide.

An object of the invention is to use small quantities at concentrations which enable accelerated lyophilization, longer predictable storage and overnight shipment, and increase worker safety. Corollary to this objective is the elimination of need for cold storage and refrigeration.

An object of the invention is to use vials with an expanded surface area, extremely cold temperatures and very low level pressures in combination to accelerate lyophilization.

An object of the invention is to use a two stage system to accelerate lyophilization by not only lowering vacuum pressure, but also, after initial removal of oxidizing agents, to extract vapor more rapidly by supercooling gas being evacuated.

An object of the invention is to create a stable vehicle for delivering selectively toxic radionuclides to target tissues.

DETAILED DESCRIPTION OF THE INVENTION

In contrast to the Wolfangel '556 invention which stated: "the lyophilization step itself generally takes about 24 hours to perform," the present invention proposes to produce a stable radiopharmaceutical complex by a lyophilization process which "freeze-dries" the complex in five hours or less, normally 2–4 hours, and then requires no further refrigeration.

The preferred mode of the invention is utilized in conjunction with Iodine-123 ("I-123" (123 being the sum of the protons and neutrons)) radionuclides. The following illustrates the compositions and processes of this invention, but is not meant to limit the scope of the invention in any way.

An I-123 labelled compound such as meta-iodo-benzyl-guanidine ("MIBG") is prepared. The concentration is increased so that ultimately one-half milliliter or less will equal one dose. For example the usual does of I-123 MIBG for a typical patient would be 10 mCi (millicuries). Because the half life is 12 hours, in order to allow for normal radioactive decay in shipment so that the dose is 10 mCi upon administration, 36 mCi would be mixed on the prior day anticipating overnight shipment.

A suitable way to reach this desired concentration would be to mix the I-123 MIBG to a concentration of 100 MCi/ml. Using sterile or aseptic technique, 0.36 ml. which is 0.36 times the starting concentration of 100 mCi would be dispensed into a 10 ml. vial.

In order to achieve the objects of this invention, and in contrast to the 24 hour lyophilization period set out in Wolfangel '556, this invention proposes to use the following apparatus. First, the vial will be stoppered with a sterile lyophilization stopper. For this invention, a lyophilization stopper is a stopper which permits flow of vapor. The preferred stopper is a "three-legged" stopper which has grooves to permit equalization of pressure between the interior of the vial and the ambient atmosphere in which the vial(s) is (are) present. A typical three legged stopper that is suitable for the invention is a three-legged n-butyl rubber lyophilization stopper 224100-202 manufactured by Wheaton Pharmaceutical of Wheaton, Ill. The vials will be placed in a tray in the shape of a standard round baking pan with a perimeter wall of about 1 inch. The vials are flat bottomed and are set in a tray which is shaped like a standard round baking pan with a perimeter wall of about 1 inch. The tray will be placed into a stoppering frame. The tray in the stoppering frame will be set in a chamber in the lyophilization apparatus. The stoppering frame will be place on an inner tube placed on top of it that can be inflated before the vacuum is broken in the chamber to force the stoppers against a flat surface farther into the vials after dehydration in order to seal the vials. Other mechanical devices are available to seal the vials.

The chamber, according to the procedure set forth below, will ultimately be used to not only receive the tray in the stoppering frame but also is designed to be sealed to enable a vacuum and other steps in the procedure to be undertaken.

The chamber is composed of a base which is a preferably a flat sheet of Lexan or acrylic material because of their strength. If the base is Lexan, it would be preferably about ½" thick and if acrylic, about 1 inch thick. The base is 14×14 inches and is larger than the open-ended acrylic cylinder of 12 inches in diameter and 18 inches high which is contemplated to be placed upon the flat sheet. The cylinder should be made of at least ¼ inch thick material. The ends of the acrylic material that are exposed are covered with a gas-tight seal usually of rubber or silicone. The purpose of the seal is to enable the cylinder to be set on the base and form a gas tight seal by the weight of the cylinder upon the seal. The chamber has a sealable port to accommodate a connection from the exterior of the chamber through a hose to the inner tube on the stoppering frame.

The lid of the chamber is also either Lexan or acrylic of sufficient strength to withstand the vacuum which will be placed upon it. If the lid is Lexan, it would be preferably about ½" thick and if acrylic, about 1 inch thick. The lid has a gas valve on the lid which enables entry of gas to flow into the chamber.

Another access port which consists of a one-inch rubber stopper is located centrally on the lid which will be used in case the gas valve fails and enable a needle to be inserted to relief the vacuum on the chamber. The rubber stopper also has situated in it an electrical connector to enable a wire connecting a thermistor probe, which will be on at least one of the vials, to be connected through the stopper to an outside monitoring device. A thermistor is the easiest among many means to measure temperature.

The bottom plate has a two inch hole in it which has an adapter connected to it to enable a hose to be connected to the base of the chamber in order to evacuate gas from the chamber which chamber will eventually be sealed. The evacuation hose is of sufficient strength to withstand the contemplated vacuum. The end of the hose which is not attached to the base of the chamber is attached to a secondary condenser which will not be initially activated. The secondary condenser will ultimately be maintained at a much colder temperature than the initially activated primary condenser. The secondary condenser is a stainless tube of approximately one inch diameter. That tube in the secondary condenser will be surrounded by supercool liquid Nitrogen that will be maintained around −196 C when the secondary condenser is activated.

A hose is connected from the secondary condenser to the primary condenser.

The primary condenser is a stainless steel pot which has a bottom with an aperture and an adapter connected to that aperture to which adapter is attached a drain hose which can be sealed. The stainless steel pot of the primary condenser is made of ¼ inch stainless steel, and can be sealed and is approximately 8 liters in volume and capable of withstanding the vacuum.

The primary condenser is surrounded by a standard refrigeration system capable of lowering the temperature to at least −40 C.

At the commencement of the lyophilization procedure, the primary condenser will have had its temperature lowered to −40 degrees C.

The condensing system is heavily insulated.

A hose runs from the top or side of the stainless steel pot of the primary condenser to the vacuum pump.

A vacuum pump capable of producing a vacuum of at least 10-4 Torr would be used to evacuate the chamber. An appropriate vacuum pump is model RV-12 available from BOCEdwards, of Wilmington, Mass.

In order to achieve the composition contemplated in this invention, the primary condensing coil is readied at or below −40 deg. C. Promptly after mixing the radiopharmaceutical composition, the vial containing the radiopharmaceutical composition, in the preferred mode the 0.36 ml. of aqueous I-123MIBG, is stoppered with the lyophilization stopper, with the lyophilization stopper in a position to permit passage of vapour. The vial and stopper will be fully sealed at the end of the process.

The vial(s) is (are) placed into the tray and a sufficient amount of liquid nitrogen is poured onto the tray in order to flash freeze the vials by the heat transfer from the aqueous I-123MIBG through the sides of the vial. Because of the small quantity which is used and the high surface area of the vial, the freezing occurs virtually instantaneously. The tray is placed into a stoppering frame in the chamber with the inner tube connected and installed so that at the end of the procedure, before the vacuum is broken, the port to the inner tube can be opened and the tube will inflate and force the stoppers fully into the vials in order to seal them.

As the liquid nitrogen evaporates off, a thermistor on one of the vials is connected to the electrical connector on the rubber stopper which connects to an outside temperature monitoring device. The liquid nitrogen is allowed to evaporate, all the while maintaining the temperature of the vial at or below −10 degrees C.

The top of the chamber is installed and forms a seal with the cylindrical side of the chamber. After evaporation of the liquid nitrogen, the gas valve on top of the chamber is closed, and the rubber stopper is installed.

After the tray containing the flash-frozen vials is placed into the chamber, and the chamber has been sealed, the vacuum pump is turned on. A vacuum pressure is first felt in the primary condenser and any vapor in the chamber begins to flow out through the secondary condenser and freezes in the primary condenser which is kept at a temperature above the boiling point of oxygen, meaning the evacuation of the sealable chamber occurs at a primary condenser temperature of approximately −40 degrees C. until the pressure sufficient to eliminate the explosive potential of liquid oxygen has reached approximately $10^{-2}$ Torr. When the vacuum pump gauge shows $10^{-3}$ Torr, usually after about 20 minutes, liquid Nitrogen at −196 degrees C. is allowed to flow through the secondary condenser and cool the stainless steel tube contained in the secondary condenser through which gas evacuated from the chamber is flowing. The very cold liquid Nitrogen in the secondary compressor is used to increase the temperature difference between the secondary condenser and the vial contents to accelerate the lyophilization. The secondary condenser is placed in series with the primary condenser and the evacuated chamber containing the tray of vials. The secondary condenser takes over as the larger and faster heat sink to capture the vaporized water.

Because the acrylic chamber has no refrigeration, the temperature of the vial and the vial contents tend to rise above 0 degrees C. after all of the water is removed. This signals the completion of the cycle. The thermistor probe connected through the rubber stopper to the outside monitoring device enables the monitoring of the vial temperature. The vials would then be sealed in partial pressure of pharmaceutically inert gas that is fully dehydrated or "dry," meaning gas that is non-reactive with the pharmaceutical composition, the gas preferably being argon or nitrogen. An inner tube will have been placed in the chamber to be inflated to force the stoppers into the vial to seal them. An auxiliary cylinder of gas that is chemically inert relative to the lyophilized radionuclide is used to gradually inflate the inner tube through the valve to force the stoppers into the vials. The vacuum is broken. The vial stoppers further secured with an aluminum seal. At the end of the process upon warming, the water which was frozen and subsequently melted will be drained from the primary condenser.

The vials are ready to be shipped with predictable half lives for the radionuclide and a stabilized ligand in powdered form.

If it is desired to accelerate the lyophilization process, inert gas may be admitted through the gas valve into the chamber to displace any oxygen and enable the secondary condenser to be turned on sooner. The displacement is necessary to prevent accumulation of liquid oxygen in the secondary condenser. In the ordinary procedure, if the secondary condenser is activated before the 10-3 level is reached, there is a risk of collecting liquid oxygen which is potentially explosive.

The secondary condenser is in series with the primary condenser, and could be located subsequent to the primary condenser in the evacuation and condensing system.

The speed of the lyophilization process is positively influenced by the lowering of the vapor pressure external to the material being dried. Secondly, the speed is positively influenced by the greater temperature difference between product being cooled and the temperature of the condenser where the water is being collected.

The lyophilized radiopharmaceutical composition is reconstituted "on site" for administration to patients by the addition of a suitable diluent to bring the radiopharmaceutical complex into solution at the time of administration to the patient.

For administration, the I-123 labelled MIBG in the vial must be reconstituted. Because of the minute quantity of material, the vial of radionuclide complex, in the preferred mode the I-123 labelled MIBG will appear empty. The MIBG ligand is stable for several days because of the absence of water which is the primary substance from which free radicals are generated by gamma ray collisions with water molecules. The gamma rays are being emitted by the radionuclide, that is the I-123. The health care provider would add up to 2 ml. of sterile normal saline. The desired dose would be withdrawn and measured in a dose calibrator of a type manufactured by Capintec of Montville, N.J. If the glass vial is measured in the dose calibrator, the person measuring the dose must recognize that the glass vial will decrease the apparent activity. Upon calibration of the desired dose, the I-123 MIBG now re-dissolved in the solution is promptly administered to the patient.

The advantages are that the flash freezing and lowering of vapor pressure result in quick formation and evaporation or sublimation (evaporation from ice to water vapour (a gas)) of water from the I-123 MIBG. The I-123 MIBG need not be shipped frozen in dry ice nor need it be shipped for overnight delivery. Shipping in dry ice over a weekend is generally not commercially practical. The I-123 MIBG can be shipped over the weekend and be used on Monday while simply maintaining it at room temperature or below.

The micro quantities involved for radionuclide complexes such as I-123 MIBG substantially reduce the exposure of production workers and health care providers because minute quantities are involved.

More generally, the preferred mode will use compounds that have a half life of one hour to a maximum of 12 hours. Longer half lives are less used because of slower radioactive decay exposing the body to increased radiation. It is generally preferable to apply the flash-freezing first because application of the reduced pressure may cause the solution to boil out of the vial.

Applying the invention more generally, the intent is to utilize the invention to produce stabilized radiopharmaceutical compositions. Such stabilized radiopharmaceutical compositions include radionuclides which are combined with ligand useful for diagnosis or diagnostic treatment or therapy to form radiopharmaceutical complexes in solution or suspension. These complexes then are lyophilized in accord with the above procedure according to the desired radioactivity level for the selected radionuclide. The form of radiopharmaceutical composition lyophilized according to this invention can be stored until needed for use. This invention allows for the central preparation, purification and shipment of a stabilized form of a radiopharmaceutical complex which merely is reconstituted prior to use. Thus, complicated or tedious formulation procedures, as well as unnecessary risk of exposure to radiation, at the site of use are avoided.

The term "radiopharmaceutical composition" includes any chemical composition including a radionuclide. Such term "radionuclide" includes cyclotron-produced radionuclides including those referenced in Table 1 on page 7 of M. Welch and C. Redvanly, Handbook of Radiopharmaceuticals: Radiochemistry and Applications (John Wiley & Sons, Ltd, Chichester, West Sussex, England 2003) (hereafter "Handbook of Radiopharmaceuticals"), Table III on p. 77 of the Handbook of Radiopharmaceuticals, and throughout chapters 1 and 2 of the Handbook of Radiopharmaceuticals. Such term "radionuclide" includes reactor-produced radionuclides including those referenced in Table 2 on page 98 of the Handbook of Radiopharmaceuticals and throughout chapter 3 of the Handbook of Radiopharmaceuticals. Radionuclide also includes radioactive isotopes of any element referenced in the Table 1 and Table 2 referenced in this paragraph, and includes Cu64 (which has traditionally not been recognized as useful), Fe, including Fe52 and 5959 and $Fe^{3+}$ radioisotopes, Yt, and Bi. Details of Gallium, Indium, and Copper radionuclides included are referenced in Tables 1 on page 264, Table 4 on page 374, and Table 1 on page 402 of the Handbook of Radiopharmaceuticals, respectively. Other useful radionuclides, which sometimes overlap those of Table 1 and Table 2 just referenced can be found for iodine radionuclides at p. 424 of the Handbook of Radiopharmaceuticals, and bromine radionuclides at p. 442 of the Handbook of Radiopharmaceuticals. The Technetium radionuclides and technetium radiopharmaceutical compositions are included. The term radiopharmaceutical composition is intended to be comprehensive because of the utility of the invention to radiopharmaceuticals and their longer-term preservation. Therefore, the term is defined to include the ligands bonded with radionuclides, compounds in which the radionuclide is integral to the ligand or compound, and compounds or mixtures in which the radionuclide is complexed. Accordingly, further amplification of the comprehensive scope of radiopharmaceutical composition is given herein.

The term "radiopharmaceutical composition" includes isotopes that are beta particle emitters, including those listed in Table 2 on page 773 of the Handbook of Radiopharmaceuticals, and Fe52, Cu64, Cu67, Ga68, Br77 and I124.

The term "radiopharmaceutical composition" includes radionuclides bonded to a ligand. For the purposes of this application, the term "ligand" is taken to mean a biocompatible vehicle, typically a molecule, capable of binding a radionuclide and rendering the radionuclide appropriate for administration to a patient. Thus, by way of illustration and not limitation, the term ligand encompasses both chelating agents capable of sequestering the radionuclide (usually a chemically-reduced form of the radionuclide) as well as carrier molecules, such as lipophilic cations with radioisotope labeling, antibodies, antibody fragments, fatty acids, amino acids or other peptides or proteins. The term radiopharmaceutical composition includes receptor specific agents, tumor agents, tumor associated antigen, antithrombotic GPIIb/IIa receptor antagonists, agents for neuroreceptors/transporters and amyhloid plaque, BZM, and monoclonal or polyclonal antibodies, particularly in Tc radiopharmaceuticals where preservation of the ligand is important (a general summary of which is on p. 349 of the Handbook of Radiopharmaceuticals). The application of the invention to compounds for assessment of multi-drug resistance status is contemplated. Chelating agents can include bifunctional and multifunctional chelates. A non-exhaustive list of chelating agents is referenced on pages 366 and page 376 of the Handbook of Radiopharmaceuticals. Included in the term ligand are antibodies bound via a chelate. Such antibodies may include monoclonal antibodies or polyclonal antibodies. Other ligands contemplated include neuroreceptor imaging agents, and receptor imaging agents, and myocardial sympathetic nerve imaging agents, many of which are referenced in Handbook of Radiopharmaceuticals. The carrier molecules often are specifically targeted at a tumor cell or tumor-specific antigen, an organ or a system of interest for observational and consequent diagnostic purposes, or in need of therapy. Carrier molecules may be directly labeled with the radionuclide, in which case any pharmaceutically acceptable counter-ion for the therapy or diagnostic intended may be used. The radionuclide may be bound to a carrier molecule via a chelate or other binding functionality. The term "complex" is taken to mean, broadly, the union of the radionuclide and the ligand to which it is attached. The chemical and physical nature of this union varies with the nature of the ligand. The invention includes compounds in the Handbook of Radiopharmaceuticals seeking receptors, including so-called antagonists which fit receptors, a partial, but fairly complete list of which is found on pages 452-457 and 717 of the Handbook of Radiopharmaceuticals.

The term "radiopharmaceutical composition" refers to a composition including the radionuclide-ligand complex as well as suitable stabilizers, preservatives and/or excipients appropriate for use in the preparation of an administrable pharmaceutical. The invention contemplates that for certain large proteins susceptible to breaking from the freezing process, such large protein structures would be supported by a lyophilization aid known to reasonably skilled practitioners in the art of pharmacy such as lactose, dextrose, albumin, gelatin or sodium chloride.

The term "radiopharmaceutical composition", includes, for therapeutic purposes, therapeutic radionuclides, including Auger electron emitters such as those described on pages 772 and 776 of the Handbook of Radiopharmaceuticals. Auger electron emitters can be useful because they can result in additional deposition of energy in tissue as to which radiopharmaceutical damage is desired. Such damage is generally desired to be minimized in diagnostic uses.

The general method of this invention, and the composition contemplated to be created can be implemented on a general basis as follows: after a radiopharmaceutical composition is prepared by known methods appropriate to the composition, aliquots of the radioactive complex are aseptically dispensed into sterile vials consistent with the procedure outlined and the radioactive product is lyophilized according to the procedure of this invention to produce the stable lyophilized powder. The virtually complete absence of water results in a substantial improvement in the stability of the preparation, from both radio chemical purity and chemical purity standpoints, versus prior preparations. The stabilized complex can be prepared several days in advance, shipped and stored until needed for use. The preferred mode of the invention is focused on radionuclides that are gamma emitters of diagnostic value and with a half-life sufficiently long to make the preparation, lyophilization and shipment of the compounds practical, but the invention is useful for alpha- and beta-emitting radionuclides.

As an example of an additional preferred mode of invention, Cu64 can be complexed with zinc isonitrile and Cu64 isonitrile can be used for PET (Positron Emission Tomography) imaging. Without the use of the process and composition of Cu64 isonitrile described herein, the half-life of Cu64 is such that its use as an imaging agent is relatively impractical. For cardiac imaging, the use of an I123 or I124 isotope in combination with a fatty acid is useful on a broader patient base than the current commonly used FDG imaging. In order to use 2-deoxy-2-[18F]fluoro-D-glucose [18FDG] for imaging the heart, the heart must be converted from fatty acid metabolism to glucose metabolism which is accomplished by feeding the patient high levels of glucose, usually three or four candy bars and waiting for approximately an hour. This is unhealthy for diabetics. This invention enables the use of shorter half-life compounds and in particular the I123 or I-124 fatty acid radiopharmaceuticals and eliminates the necessity of conversion of the heart from fatty acid metabolism to glucose metabolism. This process and the composition of the invention present a novel opportunity to use radioisotopes of shorter half-lives. I-124 radionuclides generally, and I-124 fatty acid radiopharmaceuticals can be used in conjunction with PET imaging.

Another preferred mode of invention is to use I-124 MIBG for neuroendocrine imaging and I-124 fatty acids both stabilized by the lyophilization process in this invention. Once again, only with the invention is the use of I-124 practical to sufficiently concentrate the I-124 while preserving the integrity of the overall I-124 radiopharmaceutical composition. The use of I-123 radionuclides is also made more practical by this invention, particularly in conjunction with fatty acid labeling.

At the point of use, the radiopharmaceutical compositions of the present invention are prepared for administration to a patient. Such preparation advantageously merely involves reconstitution with an appropriate diluent to bring the complex into solution. This diluent may be sterile water for injection (SWFI), dextrose and sodium chloride injection or sodium chloride (physiological saline) injection, for example. The preferred diluent is water for injection or physiological saline (9 mg/ml) which conforms to the requirements listed in the U.S. Pharmacopeia.

The present invention is particularly well suited for the preparation of stable, pre-labeled antibodies for use in the diagnosis and treatment of cancer and other diseases. For example, antibodies expressing affinity for specific tumors or tumor-associated antigens are labeled with a diagnostic radionuclide, either directly or via a bi-functional chelate, and the labeled antibodies are stabilized through lyophilization. Where a bi-functional chelate is used, it generally is covalently attached to the antibody. The antibodies used can be polyclonal or monoclonal, and the radionuclide-labeled antibodies can be prepared according to methods known in the art. The method of preparation will depend upon the type of radionuclide and antibody used. The stable, lyophilized, radio labeled antibody merely is reconstituted with suitable diluent at the time of intended use, thus greatly simplifying the on site preparation process. The process of this invention can be applied to stabilize many types of pre-labeled antibodies, including, but not limited to, polyclonal and monoclonal antibodies to tumors associated with melanoma, colon cancer, breast cancer, prostate cancer, etc. Such antibodies are known in the art and are readily available. Other ligands with specific affinities to sites in need of radiotherapy are known in the art and will continue to be discovered.

The radiopharmaceutical composition which results from the method of this invention may be further purified after reconstitution, if desired. One method of purification is described in EP 250966, noted above. Other methods are known to those skilled in the art.

The radiopharmaceutical composition can include other components, if desired. Useful additional components include chemical stabilizers, lyophilization aids and microbial preservatives. Such chemical stabilizers include ascorbic acid, gentisic acid, reductic acid, para-amino benzoic acid, and erythorbic acid among others. In some cases, these agents are beneficial in protecting the oxidation state of the radionuclide by preferential reaction with oxygen or by direct effect. The term lyophilization aids includes those substances known to facilitate good lyophilization of the product. These aids are used to provide bulk and stability to the dried pellet and include lactose, dextrose, albumin, gelatin, sodium chloride, mannitol, dextran and pharmaceutically-acceptable carriers, among others. Antimicrobial preservatives inhibit the growth of or kill microbial contaminants which are accidentally added to the product during preparation. The term antimicrobial preservatives includes methylparaben, propylparaben and sodium benzoate. These components generally are added to the composition after the complex has been formed between the ligand and the radionuclide but prior to lyophilization. Bacteriastatic agents, for example, methyl and propyl-paraben may be added. Also contemplated are the addition of solubilizing agents such as polyethylene glycol to enhance the solubility of fatty acid compounds tagged with radionuclides in normal saline solution or other water based solutions.

The above process, apparatus and resulting composition is adaptable to the stabilization and preservation of virtually all radionuclides whatever the solvent used for initial composition. Some preferred applications include stabilization of radiolabeled peptides, [18 F] deoxyglucose, radiolabelled annexin, 99mTc-annexin, radiolabelled monocyte chemoattractant protein. i.e. 125-I-(MCP-1), radiolabelled Dopamine transporter agents, (S)-N-(1-ethylpyrrolidin-2-ylmethyl)-2-hydroxy-3-iodo-6-methoxybenzamide (3-IBZM) (More generally "BZM,), (S)-N-(1-ethylpyrrolidin-2-ylmethyl)-2-hydroxy-5-iodo-6-methoxybenzamide (5-IBZM), I-123-2-beta-carbomethoxy-3-beta(4-iodophenyl) N-(3-fluro propyl) nortropane ("CIT" or "beta-CIT") and various tropane derivatives, I-123 fatty acids, particularly for cardiovascular imaging, radiolabelled octreotide or radiolabelled depreotide, HEDP (diagnostic skeletal imaging or treatment of metastatic bone pain), radiolabelled antibodies, both polyclonal and monoclonal, with selective affinities for tumor-associated antigens diagnosis or in situ radiotherapy of malignant tumors such as melanomas), and ligands with selective affinity for the hepatobiliary system (the liver-kidney system), including 2,6-dimethylacetanilideiminodiacetic acid and the family of other imidoacetic acid group-containing analogs thereof (collectively referred to herein as "HIDA agents"), mono-, di- and polyphosphoric acids and their pharmaceutically-acceptable salts including polyphosphates, pyrophosphates, phosphonates, diphosphonates and imidophosphonates. Preferred ligands are 1-hydroxyethylidene diphosphonate, methylene diphosphonate, (dimethylamino)methyl diphosphonate, methanehydroxydiphosphonate, and imidodiphosphonate (for bone-scanning and alleviation of pain); strontium 89 ethylene diamine tetramethylene phosphate, samarium 153-ethylene diamine tetramethylene phosphate, radiolabelled monoclonal antibodies, 99m-Tc HMPAO (hexamethylproplyene amine oxime), yttrium 90-labeled ibritumomab tiuxetan (Zevalin® Registered Trademark of Biogen Idec, Inc.), and meta-iodobenzyl guanidine. Ethylene diamine tetramethylene phosphate and ethylene diamine tetramethylene phosphoric acid and the pharmaceutically related mono-, di- and polyphosphoric acids and their pharmaceutically-acceptable salts including polyphosphates, pyrophosphates, phosphonates, diphosphonates and imidophosphonates are collectively called EDTMP.

Suitable radionuclides which are well-known to those skilled in the art include radioisotopes of copper, technetium-99m, rhenium-186, rhenium-188, antimony-127, lutetium-177, lanthanum-140, samarium-153, radioisotopes of iodine, indium-111, gallium-67 and -68, chromium-51, strontium-89, radon-222, radium-224, actinium-225, californium-246 and bismuth-210. Other suitable radionuclides include F-18, C-11, Y-90, Co-55, Zn-62, Fe-52, Br-77, Sr-89, Zr-89, Sm-153, Ho-166, and Tl-201.

The invention is not meant to be limited to the disclosures, including best mode of invention herein, and contemplates all equivalents to the invention and similar embodiments to the invention for humans, mammals and plant science. Equivalents include combinations with or without stabilizing agents and adjuncts that assist in reservation, and their pharmacologically active racemic mixtures, diastereomers and enantiomers and their pharmacologically acceptable salts in combination with suitable pharmaceutical carriers.

What is claimed is:

1. A method of preparing a stable rapidly lyophilized radiopharmaceutical composition for diagnostic or therapeutic purposes that needs no refrigeration upon completion of the method and that increases the predictability of the integrity of the radiopharmaceutical composition by reducing radiolysis damage, comprising the following steps:

evacuating a sealable chamber containing a flash frozen amount of said radiopharmaceutical composition having at least one radionuclide in at least one lyophilization-stoppered but as yet unsealed vial;

said evacuating of said sealable chamber occurring by a vacuum pump connected by an evacuation tube passing through a primary condenser and a secondary condenser to lower the pressure to $10^{-3}$ Torr while maintaining the temperature of said primary condenser above the boiling point of oxygen at said pressure;

activating said secondary condenser to reduce said evacuation tube temperature below the boiling point of oxygen in order to accelerate the removal of water from said sealable chamber, thereby reducing more rapidly the presence of water molecules, including radiolysis degenerated water molecules, and reducing attendant free radical damage to said radiopharmaceutical composition, and increasing the predictability of the integrity of the radiopharmaceutical composition;

restoring the ambient pressure in the sealable chamber to approximately atmospheric pressure with a pharmaceutically inert gas upon completion of the desired removal of water, and sealing the said at least one vial in order to preclude entry of external fluid upon such restoring of ambient pressure.

2. The method according to claim 1, further comprising: said evacuating said sealable chamber occurring at a primary condenser temperature of approximately −40 degrees C. until said pressure sufficient to eliminate the explosive potential of liquid oxygen has reached approximately $10^{-2}$ Torr.

3. The method according to claim 2, further comprising: said radiopharmaceutical composition having at least one ligand.

4. The method according to claim 3, further comprising: said at least one ligand being selected from the group of BZM, Beta-CIT, EDTMP, HIDA or fatty acids.

5. The method according to claim 3, further comprising: said radiopharmaceutical composition having the ligand MIBG.

6. The method according to claim 2, further comprising: said radiopharmaceutical composition having at least one monoclonal antibody in combination with at least one lyophilization aid for providing structural stabilization in combination with said at least one monoclonal antibody.

7. The method according to claim 2, further comprising: said radiopharmaceutical composition having at least one peptide in combination with at least one lyophilization aid for providing structural stabilization in combination with said at least one peptide.

8. The method according to claim 2, further comprising: said radiopharmaceutical composition having at least one molecular recognition unit in combination with at least one lyophilization aid for providing structural stabilization in combination with said at least one molecular recognition unit.

9. The method according to claim 2, further comprising: said at least one radionuclide being selected from the group of F-18, C-11, Y-90, I-123, I-124, I-125, I-131, Cu-64, Cu-67, Co-55, Zn-62, Fe-52, Ga-64, Ga-67, Ga-68, Br-77, Sr-89, Zr-89, Tc-99m, In-111, Sm-153, Ho-166, Lu-177, Re-186, and Tl-201.

10. The method according to claim 9, further comprising: said radiopharmaceutical composition having at least one ligand.

11. The method according to claim 10, further comprising: said at least one ligand being selected from the group of BZM, Beta-CIT. EDTMP, HIDA or fatty acids.

12. The method according to claim 10, further comprising: said radiopharmaceutical composition having the ligand MIBG.

13. The method according to claim 9, further comprising: said radiopharmaceutical composition having at least one monoclonal antibody in combination with at least one lyophilization aid for providing structural stabilization in combination with said at least one monoclonal antibody.

14. The method according to claim 9, further comprising: said radiopharmaceutical composition having at least one peptide in combination with at least one lyophilization aid for providing structural stabilization in combination with said at least one peptide.

15. The method according to claim 9, further comprising: said radiopharmaceutical composition having at least one molecular recognition unit in combination with at least one lyophilization aid for providing structural stabilization in combination with said at least one molecular recognition unit.

16. The method according to claim 1, further comprising: said radiopharmaceutical composition having at least one ligand.

17. The method according to claim 16, further comprising:
said at least one ligand being selected from the group of BZM, Beta-CIT, EDTMP, HIDA or fatty acids.

18. The method according to claim 16, further comprising:
said radiopharmaceutical composition having the ligand MIBG.

19. The method according to claim 1, further comprising:
said radiopharmaceutical composition having at least one monoclonal antibody in combination with at least one lyophilization aid for providing structural stabilization in combination with said at least one monoclonal antibody.

20. The method according to claim 1, further comprising:
said radiopharmaceutical composition having at least one peptide in combination with at least one lyophilization aid for providing structural stabilization in combination with said at least one peptide.

21. The method according to claim 1, further comprising:
said radiopharmaceutical composition having at least one molecular recognition unit in combination with at least one lyophilization aid for providing structural stabilization in combination with said at least one molecular recognition unit.

22. The method according to claim 1, further comprising:
said at least one radionuclide being selected from the group of F-18, C-11, Y-90, I-123, I-124, I-125, I-131, Cu-64, Cu-67, Fe-52, Co-55, Zn-62, Ga-64, Ga-67, Ga-68, Br-77, Sr-89, Zr-89, Tc-99m, In-111, Sm-153, Ho-166, Lu-177, Re-186, and Tl-201.

23. The method according to claim 22, further comprising:
said radiopharmaceutical composition having at least one ligand.

24. The method according to claim 23, further comprising:
said at least one ligand being selected from the group of BZM, Beta-CIT. EDTMP, HIDA or fatty acids.

25. The method according to claim 23, further comprising:
said radiopharmaceutical composition having the ligand MIBG.

26. The method according to claim 22, further comprising:
said radiopharmaceutical composition having at least one monoclonal antibody in combination with at least one lyophilization aid for providing structural stabilization in combination with said at least one monoclonal antibody.

27. The method according to claim 22, further comprising:
said radiopharmaceutical composition having at least one peptide in combination with at least one lyophilization aid for providing structural stabilization in combination with said at least one peptide.

28. The method according to claim 22, further comprising:
said radiopharmaceutical composition having at least one molecular recognition unit in combination with at least one lyophilization aid for providing structural stabilization in combination with said at least one molecular recognition unit.

29. A method of preparing a stable rapidly lyophilized radiopharmaceutical composition for diagnostic or therapeutic purposes that needs no refrigeration upon completion of the method and that increases the predictability of the integrity of the radiopharmaceutical composition by reducing radiolysis damage, comprising the following steps:
evacuating a sealable chamber containing a flash frozen amount of said radiopharmaceutical composition having at least one radionuclide in at least one lyophilization-stoppered but as yet unsealed vial;
said evacuating of said sealable chamber occurring by a vacuum pump through an evacuation tube passing through a secondary condenser to a primary condenser to lower the pressure to $10^{-3}$ Torr while maintaining the temperature of said primary condenser above the boiling point of oxygen;
activating said secondary condenser to reduce said evacuation tube temperature below the boiling point of oxygen in order to accelerate the removal of water from said sealable chamber thereby reducing more rapidly the presence of water molecules, including radiolysis degenerated water molecules, and reducing attendant free radical damage to said radiopharmaceutical composition, and increasing the predictability of the integrity of the radiopharmaceutical composition; and
restoring the ambient pressure in the sealable chamber to approximately atmospheric pressure with a pharmaceutically inert gas upon completion of the desired removal of water;
sealing said at least one vial in order to preclude entry of external fluid upon such restoration of ambient pressure.

30. The method according to claim 1, further comprising:
said evacuating said sealable chamber occurring at a primary condenser temperature of approximately −40 degrees C. until said pressure sufficient to eliminate the explosive potential of liquid oxygen has reached approximately $10^{-2}$ Torr.

31. The method according to claim 30, further comprising:
said radiopharmaceutical composition having at least one ligand.

32. The method according to claim 31, further comprising:
said at least one ligand being selected from the group of BZM, Beta-CIT, EDTMP, HIDA or fatty acids.

33. The method according to claim 31, further comprising:
said radiopharmaceutical composition having the ligand MIBG.

34. The method according to claim 30, further comprising:
said radiopharmaceutical composition having at least one monoclonal antibody in combination with at least one lyophilization aid fur providing structural stabilization in combination with said at least one monoclonal antibody.

35. The method according to claim 30, further comprising:
said radiopharmaceutical composition having at least one peptide in combination with at least one lyophilization aid for providing structural stabilization in combination with said at least one peptide.

36. The method according to claim 30, further comprising:
said radiopharmaceutical composition having at least one molecular recognition unit in combination with at least one lyophilization aid for providing structural stabilization in combination with said at least one molecular recognition unit.

37. The method according to claim 30, further comprising:
said at least one radionuclide being selected from the group of F-18, C-11, Y-90, I-123, I-124, I-125, I-131, Cu-64, Cu-67, Co-55, Zn-62, Fe-52, Ga-64, Ga-67, Ga-68, Br-77, Sr-89, Zr-89, Tc-99m, In-111, Sm-153, Ho-166, Lu-177, Re-186, and Tl-201.

38. The method according to claim 37, further comprising:
said radiopharmaceutical composition having at least one ligand.

39. The method according to claim 38, further comprising:
said at least one ligand being selected from the group of BZM, Beta-CIT, EDTMP, HIDA or fatty acids.

40. The method according to claim 38, further comprising:
said radiopharmaceutical composition having the ligand MIBG.

41. The method according to claim 37, further comprising:
said radiopharmaceutical composition having at least one monoclonal antibody in combination with at least one lyophilization aid for providing structural stabilization in combination with said at least one monoclonal antibody.

42. The method according to claim 37, further comprising:
said radiopharmaceutical composition having at least one peptide in combination with at least one lyophilization aid for providing structural stabilization in combination with said at least one peptide.

43. The method according to claim 37, further comprising:
said radiopharmaceutical composition having at least one molecular recognition unit in combination with at least one lyophilization aid for providing structural stabilization in combination with said at least one molecular recognition unit.

44. The method according to claim 29, further comprising:
said radiopharmaceutical composition having at least one ligand.

45. The method according to claim 44, further comprising:
said at least one ligand being selected from the group of BZM, Beta-CIT, EDTMP, HIDA or fatty acids.

46. The method according to claim 44, further comprising:
said radiopharmaceutical composition having the ligand MIBG.

47. The method according to claim 29, further comprising:
said radiopharmaceutical composition having at least one monoclonal antibody in combination with at least one lyophilization aid for providing structural stabilization in combination with said at least one monoclonal antibody.

48. The method according to claim 29, further comprising:
said radiopharmaceutical composition having at least one peptide in combination with at least one lyophilization aid for providing structural stabilization in combination with said at least one peptide.

49. The method according to claim 29, further comprising:
said radiopharmaceutical composition having at least one molecular recognition unit in combination with at least one lyophilization aid for providing structural stabilization in combination with said at least one molecular recognition unit.

50. The method according to claim 29, further comprising:
said at least one radionuclide being selected from the group of F-18, C-11, Y-90, I-123, I-124, I-125, I-131, Cu-64, Cu-67, Fe-52, Co-55, Zn-62, Ga-64, Ga-67, Ga-68, Br-77, Sr-89, Zr-89, Tc-99m, In-111, Sm-153, Ho-166, Lu-177, Re-186, and Tl-201.

51. The method according to claim 50, further comprising:
said radiopharmaceutical composition having at least one ligand.

52. The method according to claim 51, further comprising:
said at least one ligand being selected from the group of BZM, Beta-CIT, EDTMP, HIDA or fatty acids.

53. The method according to claim 51, further comprising:
said radiopharmaceutical composition having the ligand MIBG.

54. The method according to claim 50, further comprising:
said radiopharmaceutical composition having at least one monoclonal antibody in combination with at least one lyophilization aid for providing structural stabilization in combination with said at least one monoclonal antibody.

55. The method according to claim 50, further comprising:
said radiopharmaceutical composition having at least one peptide in combination with at least one lyophilization aid for providing structural stabilization in combination with said at least one peptide.

56. The method according to claim 50, further comprising:
said radiopharmaceutical composition having at least one molecular recognition unit in combination with at least one lyophilization aid for providing structural stabilization in combination with said at least one molecular recognition unit.

57. The method according to any one of claims 1 through 56, further comprising:
said radiopharmaceutical composition being an imaging agent selected from the group of imaging agents having a selective affinity for the hepatobiliary system.

58. The method according to any one of claims 1 through 56, further comprising:
said radiopharmaceutical composition being an imaging agent selected from the group of imaging agents having a selective affinity for the cardiac system.

59. The method according to any one of claims 1 through 56, further comprising:
said radiopharmaceutical composition being an imaging agent selected from the group of imaging agents having a selective affinity for the cerebral system.

60. The method according to any one of claims 1 through 56, further comprising:
said radiopharmaceutical composition being an imaging agent selected from the group of imaging agents having a selective affinity for the skeletal system.

61. The method according to any one of claims 1 through 56, further comprising:

said radiopharmaceutical composition being an imaging agent selected from the group of imaging agents used for prostate imaging.

62. The method according to any one of claims 1 through 56, further comprising:
said radiopharmaceutical composition being an imaging agent selected from the group of imaging agents used for pulmonary imaging.

63. The method according to any one of claims 1 through 56, further comprising:
said radiopharmaceutical composition having at least one lyophilization aid.

64. The method according to any one of claims 1 through 56, further comprising:
said radiopharmaceutical composition having at least one chemical stabilizer.

65. The method according to any one of claims 1 through 56, further comprising:
said radiopharmaceutical composition having at least one bacteriastatic agent.

66. The method according to any one of claims 1 through 56, further comprising:
said radiopharmaceutical composition having at least one antimicrobial preservative.

67. The method according to any one of claims 1 through 56, further comprising:
said radiopharmaceutical composition having at least one solubilizing agent.

* * * * *